| United States Patent [19] | [11] 3,976,547 |
|---|---|
| McAleer et al. | [45] Aug. 24, 1976 |

[54] CELL AND VACCINE PRODUCTION

[75] Inventors: William J. McAleer, Ambler, Pa.; Raymond E. Spier, Guildford, England; Abner J. Schlabach, Perkasie, Pa.

[73] Assignee: Merck & Co., Inc., Rahway, N.J.

[22] Filed: Nov. 19, 1974

[21] Appl. No.: 525,270

Related U.S. Application Data

[63] Continuation-in-part of Ser. No. 219,945, Jan. 24, 1972, abandoned.

[52] U.S. Cl. ............................ 195/127; 195/1.7
[51] Int. Cl.² ................................ C12K 9/00
[58] Field of Search ............ 195/127, 139, 142; 148/126; 3/1

[56] References Cited
UNITED STATES PATENTS

| 2,752,666 | 7/1956 | Goetzel et al. | 148/126 |
|---|---|---|---|
| 2,771,398 | 11/1956 | Snyder | 195/139 |
| 3,145,120 | 8/1964 | Cheroff et al. | 148/126 |
| 3,268,368 | 8/1966 | Mackiw et al. | 148/126 |
| 3,276,919 | 10/1966 | Todd | 148/126 |
| 3,281,307 | 10/1966 | Moeller et al. | 195/142 |
| 3,407,120 | 10/1968 | Weiss et al. | 195/142 |
| 3,493,651 | 2/1970 | Sloane | 424/89 |
| 3,605,123 | 9/1971 | Hahn | 3/1 |
| 3,690,961 | 9/1972 | Berghezan | 148/126 |

OTHER PUBLICATIONS

Galante et al., Journal of Bone & Joint Surgery, vol. 53A, No. 1, pp. 101–114 (Jan. 1971).

*Primary Examiner*—Alvin E. Tanenholtz
*Attorney, Agent, or Firm*—Donald J. Perrella; Julian S. Levitt; J. Jerome Behan

[57] ABSTRACT

Cell growth surfaces having controlled surface topography which permits the optimization of the fit between the cells and the growth surface. These surfaces may be constructed from sintered or sputtered titanium, glass, ceramic, plastic, or stainless steel, or may consist of a substrate having microspheres adhered to the surface thereof.

8 Claims, No Drawings

CELL AND VACCINE PRODUCTION

This application is a continuation-in-part of copending United States application Ser. No. 219,945 filed Jan. 24, 1972 and now abandoned.

More particularly, this invention relates to cell culture systems including Brockway bottles, roller bottles and multiplate propagators possessing cell growth surfaces having controlled surface topography which permits the optimization of fit between the cells and the cell growth surface resulting in increased efficiency and a decrease in the cost of vaccine production.

Human and animal vaccines are commercially produced by growing the desired virus in primary cells which must be grown on surfaces. Commercial processes were initially developed in Brockway bottles which required the use of hundreds of thousands of individual bottles to achieve production of sufficient quantities of vaccine. The use of such a large number of bottles or production units is very time consuming and costly and creates a substantial risk of contamination. As production techniques evolved, the original Brockway bottles were replaced by roller bottles which only slightly reduced the number of bottles and the handling problems associated therewith.

Mass culture systems have been developed, such as the multiplate unit disclosed in U.S. Pat. No. 3,407,120 and the Biotec rotating titanium disc apparatus, but these units present only minimal advantages over the original individual bottle system.

We have discovered that by controlling the surface topography of the cell growth surface, one can dramatically increase the yields of cells. Typical cells are microscopic in size, having a diameter of approximately 10 microns. For example the diameter of chick and duck cells may vary from about 10 to 20 microns, whereas the dimensions of WI-38 cells comprise a length of from 130 – 65 microns and a width of from 25 – 12.5 microns. By changing the surface topography from an essentially flat surface to one having irregularities which are greater in size than the diameter of the cells, the cells can be made to conform to the contours of the cell growth surface rather than over the tops of the irregularities in an essentially flat plain. The cell growth surfaces of this invention have greatly increased surface area per unit of planar area. This increased surface area per unit of planar area can be obtained by using sintered or sputtered metal such as titanium, stainless steel or aluminum, glass, ceramic, or plastic as the cell growth surface, or by coating substrates with a plurality of microspheres of the above substances.

An advantage of the present invention is the ability to produce large quantities of vaccine in Brockway bottles, roller bottles, concentric ring machines, or multiplate propagators having a substantially smaller volume than the prior art devices thereby substantially reducing the cost and complexity of the production process.

A further advantage of the surfaces of this invention is that the cell sheets are more tenaciously held and maintained longer than those produced by conventional techniques.

The surfaces of this invention may be used to grow a wide variety of primary cells, as for example, chick embryo fibroblasts, green monkey kidney, bovine kidney, or dog kidney cells, diploid cells such as WI-38 and stable live cells such as VERO, BSC, or Hela cells. Primary cultures grown on these surfaces will support the generation of typical virus vaccines, as for example measles, mumps, rubella, parainfluenza, and Mareks vaccines.

Standard growth media, sera and temperatures may be used when the surfaces of this invention are employed in the production of cells and vaccines.

EXAMPLE 1

36 $cm^2$ sintered titanium plates are immersed in 40 ml of media consisting of 50% F 10, 40% 199, 5% tryptose phosphate broth and 5% calf serum. Trypsinized chick embryo fibroblasts are suspended in the media at a concentration of $5 \times 10^5$ cells per centimeter square of surface area. The unit is held at 36.5°C in a $CO_2$ incubator for 3 days during which time the initially plated cells spread over the surface forming a cell sheet.

EXAMPLE 2

A 3 l. tank operating with 50 circular sintered titanium plates is completely filled with a slurry of trypsinized chick embryo fibroblasts suspended in a medium consisting of 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh chick cells and returned to the tank. The tank is rotated through 180° so that the lower side of the plates become the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The cells are recovered from the tank by draining the growth fluid, followed by the addition of a solution of trypsin which strips the cells from the plates. Draining this final fluid yields a usable cell slurry. The trypsin can be inactivated with calf serum to prevent cell destruction.

EXAMPLE 3

A 3 l. tank operating with 50 circular sputtered titanium plates is completely filled with a slurry of trypsinized chick embryo fibroblasts suspended in a medium consisting of 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh chick cells and returned to the tank. The tank is rotated through 180 degrees so that the lower side of the plates becomes the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The unit is then washed with Hank's solution and mumps virus in media 199 with 25% of SPGA is added to infect the cell sheet. After 96 hours this fluid is drained from the unit. The fluid obtained may be used as a mumps vaccine.

EXAMPLE 4

A 3 l. tank operating with 50 circular sintered glass plates is completely filled with a slurry of trypsinized duck embryo fibroblasts suspended in a medium consisting of media 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh duck cells and returned to the tank. The tank is rotated through 180° so that the lower side of the plates becomes the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The unit is then washed with Hank's solution and rubella virus in media 199 with 25% of SPGA is added to infect the cell sheet. After 96 hours this fluid is drained from the unit. The fluid obtained may be used as a rubella vaccine.

EXAMPLE 5

A 3 l. tank operating with 50 circular sintered plastic plates is completely filled with a slurry of trypsinized green monkey kidney cells suspended in a medium consisting of media 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh green monkey kidney cells and returned to the tank. The tank is rotated through 180° so that the lower side of the plates becomes the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The cells are recovered from the tank by draining the growth fluid followed by the addition of a solution of trypsin which strips the cells from the plates. Draining this final fluid yields a usable cell slurry. The trypsin can be inactivated with calf serum to prevent cell destruction.

EXAMPLE 6

A 3 l. tank operating with 50 circular sintered stainless steel plates is completely filled with a slurry of VERO cells suspended in a medium consisting of 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh VERO cells and returned to the tank. The tank is rotated through 180° so that the lower side of the plates becomes the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The cells are recovered from the tank by draining the growth fluid, followed by the addition of a solution of trypsin which strips the cells from the plates. Draining this final fluid yields a usable cell slurry. The trypsin can be inactivated with calf serum to prevent cell destruction.

EXAMPLE 7

A 3 l. tank operating with 50 circular sintered titanium plates is completely filled with a slurry of WI-38 cells suspended in a medium consisting of EBME with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh WI-38 cells and returned to the tank. The tank is rotated through 180° so that the lower side of the plates becomes the upper. The new cells are allowed to plate for 3 hours.

1.5 l. of fluid is removed, the unit is rotated through 90° to bring the plate perpendicular to the work surface and the plates are rotated about the center axis so that the plated cells pass through the growth media and are aerated in a cyclical manner. The operation is continued for 72 hours until complete cell sheets are formed. The cells are recovered from the tank by draining the growth fluid, followed by the addition of a solution of trypsin which strips the cells from the plates. Draining this final fluid yields a usable cell slurry. The trypsin can be inactivated with calf serum to prevent cell destruction.

EXAMPLE 8

A 3 l. tank operating with 50 circular sintered titanium plates is completely filled with a slurry of green monkey kidney cells suspended in a medium consisting of 199 with 45ml of 2.8% $NaHCO_3$ per liter and containing 10% fetal calf serum. The unit is held such that the plates are parallel to the work surface and the cells settle onto the surface for 3 hours. Following this the fluid is drained, mixed with fresh green monkey kidney cells and returned to the tank. The tank is rotated through 180° so that the lower side of the plates becomes the upper. The new cells are allowed to plate for 3 hours.

Approximately 1.5 l. of fluid is removed, the unit is rotated through 90° plate bring the plater perpendicular to the work surface and the plates are rotated about the center axis so that the plated cells pass through the growth media and are aerated in a cyclical manner. The operation is continued for 72 hours until complete cell sheets are formed. The unit is then washed with Hank's solution and parainfluenza virus in media 199 with 25% of SPGA is added to infect the cell sheet. After 96 hours this fluid is drained from the unit. The fluid obtained may be used as a parainfluenza vaccine.

What is claimed is:

1. In an in vitro cell culture container apparatus wherein cells are grown on solid metallic cell growth surfaces of said apparatus, the improvement comprising solid metallic cell growth surfaces having controlled surface topography such that the surface has irregularities which are greater than the diameter of the cells.

2. A cell culture container apparatus as in claim 1 wherein the metallic cell growth surface is sintered or sputtered metal.

3. A cell culture container apparatus as in claim 2 wherein the metallic cell growth surface is sintered titanium.

4. A cell culture container apparatus as in claim 2 wherein the metallic cell growth surface is sputtered titanium.

5. A cell culture container apparatus as in claim 2 wherein the metallic cell growth surface is sintered stainless steel.

6. A cell culture container apparatus as in claim 2 wherein the metallic cell growth surface is sputtered stainless steel.

7. A cell culture container apparatus as in claim 2 wherein the metallic cell growth surface is sintered aluminum.

8. A cell culture container apparatus as in claim 2 wherein the metallic cell growth surface is sputtered aluminum.

* * * * *